United States Patent [19]
Olsen

[11] Patent Number: 4,553,938
[45] Date of Patent: Nov. 19, 1985

[54] LOW TORSIONAL RESTRAINT INSTRUMENT HANDPIECE HOSE

[75] Inventor: Robert A. Olsen, Palatine, Ill.

[73] Assignee: Sybron Corporation, Rochester, N.Y.

[21] Appl. No.: 550,343

[22] Filed: Nov. 10, 1983

[51] Int. Cl.$^4$ ............................................. A61C 1/08
[52] U.S. Cl. ..................................... 433/126; 433/78
[58] Field of Search ................... 433/126, 82, 29, 78; 285/168, 137 R, 136

[56] References Cited

U.S. PATENT DOCUMENTS

| | | | |
|---|---|---|---|
| 3,921,296 | 11/1975 | Harris | 433/126 |
| 3,985,167 | 10/1976 | Roqoe | 285/136 |
| 4,182,038 | 1/1980 | Fleer | 433/126 |
| 4,341,518 | 7/1982 | Wallace | 433/29 |

Primary Examiner—Robert Peshock
Attorney, Agent, or Firm—Robert A. Gerlach; Robert J. Bird

[57] ABSTRACT

A hose having multiple conduits or conductors for transmitting drive air, water, chip air, light and/or electricity to a turbine-driven dental handpiece or other tool and for conveying exhaust air away from that handpiece, such hose being equipped with a plurality of swivel connectors for permitting the handpiece to be rotated a limited amount in each direction about its longitudinal axis with no objectionable restraint imposed, or restorative force exerted, by the conduits as they twist about each other during such handpiece rotation. In each disclosed embodiment, a plurality of the conduits have at least adjacent portions unattached to each other and individually provided with separate swivel connections. The disclosure also sets forth details of the low torque swivel connectors having self-energizing or other seals, a stop ring for limiting the extent of rotation of an outer tube encasing the conduits, and a means for preventing sharp bends in the outer tube that might otherwise interfere with the internal swiveling and twisting of the conductors.

3 Claims, 24 Drawing Figures

LOW TORSIONAL RESTRAINT INSTRUMENT HANDPIECE HOSE

BACKGROUND AND SUMMARY

Hoses for air-driven dental handpieces are commonly of two types. One type is extruded from a relatively soft and flexible polymeric material and provides a multiplicity of connected parallel conduits for transmitting drive air, exhaust air, chip air, and water. One such commercially available hose provides four conduits for fluid transmission and, in addition, a fifth conduit which may contain a fiberoptic waveguide (for the transmission of light to an illuminator located at the head of a handpiece) or electrical leads (for transmitting electrical energy to a light source provided by the handpiece). A second type of hose consists essentially of a flexible outer tube, often cloth-covered, containing a plurality of separate conduits or conductors for air, water, light, and/or electricity.

Both types of hoses resist twisting with torsional forces that may be sufficient to present objectionable interference to certain manipulative actions of a handpiece in use. In an effort to minimize such restraints, and the spring-like torsional restoring forces that develop when twisting does occur, dentists commonly check to make certain that a substantial length of hose has been extended and is in an untwisted or neutral state as the instrument is moved into a position for cutting, polishing, or other function the dentist selects. Even so, limited rotation of the handpiece about its longitudinal axis as it is manipulated in use does tend to be restrained to a noticeable extent by a typical multiple-conduit hose, and, even more significantly and a more onerous and fatiguing load on the operator, the restoring forces continually exerted by such a hose when it is twisted may further interfere with handpiece manipulation.

Efforts to reduce such problems have included swivel couplings of the type disclosed in co-owned U.S. Pat. No. 3,173,207 and in patents 3,936,940, 3,894,338, 4,217,101, 2,442,033, 4,213,243, 4,251,212, and 4,303,392. All of such constructions achieve unlimited swivel action at the price of increased structural complexity and manufacturing costs. In general, such a swivel coupling typically consists of male and female elements with multiple longitudinal passages that are maintained in selective communication with each other by a plurality of radial passages and annular channels isolated by sealing rings.

This invention is concerned with a relatively simple swivel arrangement for dental handpiece hoses in which the resistance to handpiece rotation about its longitudinal axis, caused in part by the multiple conduits twisting about each other, and the restorative forces exerted by such a hose when so twisted, may be greatly reduced if, first of all, at least adjacent portions of such conduits are unattached to each other for a substantial stretch (generally at least three inches), so that such unattached portions may flex independently with respect to the other conduits and, second, if a plurality of such separate distal portions are provided with individual swivel connectors. In such a construction, when the handpiece hose is twisted so that the multiple conduits or conductors become coiled about each other, each conduit nevertheless rotates at its own swivel connection and, because of such separate swivel action and rotational freedom, the resistance to twisting is reduced, and even more important the restorative action of the hose is substantially eliminated. Therefore, and especially for handpiece rotations which are normally limited to less than one full turn in either direction, the hose construction of this invention constitutes a relatively simple, low-cost, and highly effective arrangement for reducing to a low level the twisting forces required to rotate the handpiece and to an insignificant level the torsional restoring forces that would otherwise develop as a hose is twisted during ordinary handpiece operation.

It has also been found that such improvements may be achieved in a dental handpiece hose where only the larger conduits (the term "conduits" being used herein to mean fluid-transmitting tubes as well as electrical and light transmitting lines) are equipped with swivels. In general, the conduits requiring individual swivels are those used for transmitting drive air, light, and exhaust air. Other tubes, such as those for chip air and coolant water, are relatively small in diameter and have relatively little torsional stiffness and spring-like effect. Since therefore a separate swivel connection for the water line has been found unnecessary, the problems of developing a low torque dynamic seal in a swivel connection for the water passage are avoided.

The swivel connectors for all fluid conduits have low torque characteristics (under 0.5 inch ounces, and preferably under 0.2 inch ounces) and self-energizing fluid seals. Such seals are adjustable during factory assembly by compressing the elastomeric sealing ring with a retainer collar until the desired balance between torque and sealing capability is achieved, it being recognized that small leaks of drive air or exhaust air to atmosphere may be unobjectionable.

In one embodiment of the invention, the multiple conduits are contained within an outer tube, the outer tube in turn being equipped with its own swivel coupling to the handle of a dental handpiece. Such swivel coupling, like the swivel connectors for the individual conduits contained within the outer tube, may be provided with a self-energizing seal, especially if the outer tube, which is substantially larger in diameter than all of the conductors extending therethrough, is utilized for the transmission of exhaust air. Also, such embodiment may include a helical spring or liner disposed within the outer tube to give shape retention to the cross-section and to prevent sharp bends and lumen constriction that might reduce the free swivel action of the separate conductors extending through that outer tube. A further modification of this aspect of the invention may include a corrugated or other outer tube which is bendable without flattening, without the use of a spring or liner.

Other features, advantages, and objects of the invention will become apparent from the specification and drawings.

3

DETAILED DESCRIPTION OF PREFERRED EMBODIMENTS

Referring to FIGS. 1-8, the numeral 10 generally designates an air-driven turbine-powered dental handpiece connected to hose 11. The handpiece is of the contra-angle type having a head 12 and an elongated handle 13; however, it is to be understood that other types of dental handpieces such as the so-called straight handpieces, may be used.

In this specification, the geometry and relative placement of hose 11 and all of its conduits are sometimes described with reference to a "source end" and a "handpiece end" "working end" or "handpiece portion." These are simply relative terms to provide a frame of reference as an aid in describing the invention and its environment. "Handpiece end" or "working end" means the end connected to a handpiece or other tool; "handpiece portion" means the portion adjacent to or nearer to the handpiece than some other portion. "Source end" means the opposite end, toward or connected to apparatus such as a console, supply, or drain.

Figures 1, 2, 3, 4, 5:
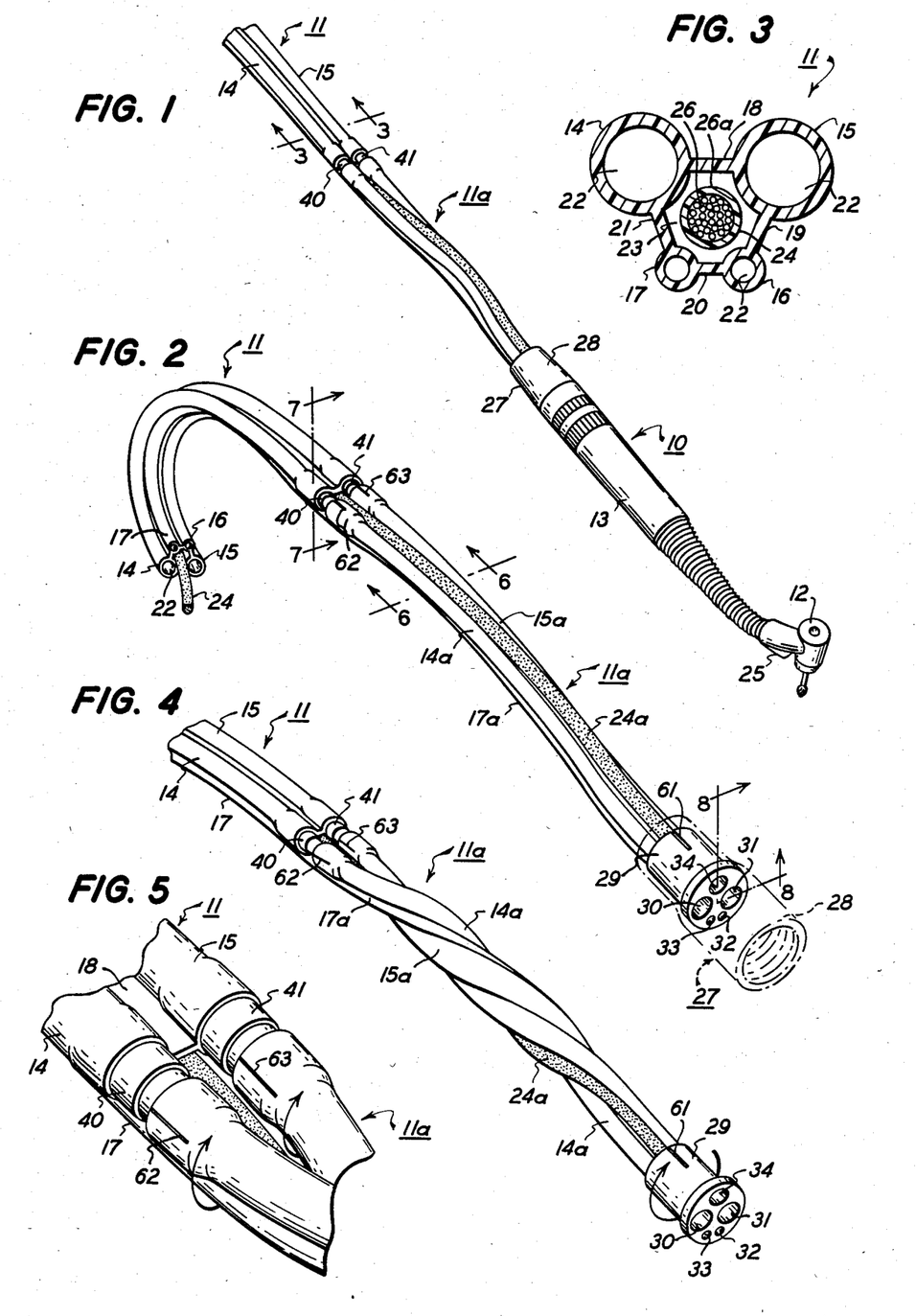
FIG. 1 is a perspective view of a dental handpiece coupled to a hose embodying the present invention.
FIG. 2 is an enlarged perspective view illustrating the handpiece end of the hose with the handpiece disconnected therefrom and with the coupling sleeve shown in phantom.
FIG. 3 is a greatly enlarged cross sectional view taken along line 3—3 of FIG. 1.
FIG. 4 is a perspective view similar to FIG. 2 but showing the handpiece end of the hose when the handpiece coupling has been rotated one full turn.
FIG. 5 is an enlarged fragmentary perspective view showing details of the structure depicted in FIG. 4.
Figure 6:
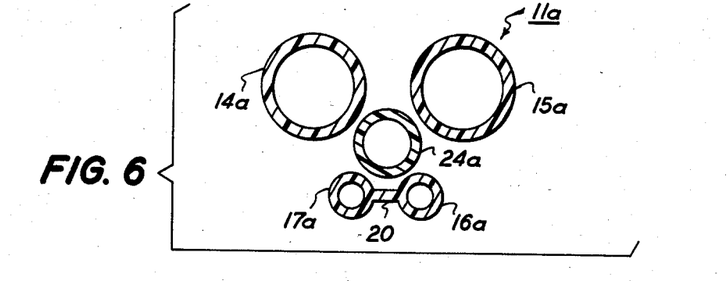
FIG. 6 is a greatly enlarged cross sectional view taken along line 6—6 of FIG. 2.

Hose 11 is elongated and has a source end (not shown) adapted for connection to a console or other dental unit equipped to supply air and water to the handpiece. FIG. 3 depicts a typical cross section in which the hose is shown to have a body composed of four connected conduits, each conduit taking the form of a flexible tubular casing 14–17 with the casings joined together by integral webs 18–21. Each casing provides a passage or channel 22, and wall portions of those casings, together with webs 18–21, define a fifth passage or channel 23. Depending on the preferences of the user and the type of handpiece to which the hose is connected, channel 23 may be left empty or may contain some transmission means used in conjunction with handpiece operation. For example, wires for the operation of a light source mounted on or within handpiece 10 may extend through the passage 23. In the particular embodiment illustrated, a fiberoptic cable 24 extends through the central passage for transmitting light to the illuminator 25 adjacent the head of the handpiece. The cable includes a bundle of light-transmitting fibers 26 ensheathed in a flexible plastic casing 26a.

The tubular casings 14–17 and webs 18–21 may be formed integrally by a suitable extrusion process as is well known in the art. The material should be flexible, soft, durable, and resilient. Thermoplastic materials having some elastomeric properties such as PVC and polyurethane have been found suitable, but other materials having similar properties are known and may be used. It is to be understood that the hose structure as shown in FIG. 3 and as described to this point is commercially available and well known. In the commercial product, the passage 22 of tubular casing 14 is used for transmitting drive air and that of casing 15 is used for exhaust air. Tubular casings 16 and 17 are used for chip air and water, respectively. Although hose 11 has a distinctive cross sectional configuration, it will also be apparent that such configuration is not critical for purposes of this invention and that other multi-passage handpiece hoses having different cross sectional configurations might be used.

The handpiece end of the hose is equipped with a coupling 27 for threadedly connecting the hose to the handle portion 13 of handpiece 10. The coupling includes an internally threaded coupling sleeve 28 and a flange-equipped cylindrical body 29 disposed within that sleeve (FIG. 2). The body 29 has a plurality of parallel and longitudinally-extending bores or openings 30, 31, 32, 33, and 34 for drive air, exhaust air, chip air, water, and light, respectively. All of the bores communicating with fluid passages of the hose may be provided with conventional tubular barb fittings 35 as shown most clearly in FIG. 8. When the coupling sleeve 28 is threaded onto the rear end of handpiece 10, the flanged end of body 29 is held firmly against the handpiece and various connector tubes of the handpiece enter the flow passages 30–33 of body 29 to place those passages in communication with the various conductor tubes or conduits of hose 11.

Hose 11 includes a handpiece portion 11a that extends from coupling 27 rearward toward the source end for a length of typically 3 to 6 inches. It will be noted from the drawings, particularly FIG. 6, that along this handpiece portion of the hose most (if not all) of the webs are omitted. Specifically, the handpiece portions 14a and 15a of the larger fluid conductors or conduits are free of attachment to each other and to any of the other conductors. The omission of the webs along this portion of the hose eliminates most of the additive torsional stiffness and spring-like restorative action that would otherwise result from ganging those portions of the conduits together. As a result, these portions of conduits 14a and 15a, and 24a of the light conductor 24, are free to flex at least to a limited extent independently of each other. The corresponding portions 16a and 17a of the chip air and water conduits are connected together for joint flexure but they too are free to flex independently of conduits 14a, 15a, and 24a.

In addition, the handpiece portions of at least two of the conductors or conduits, and preferably all of the major conductors (in this instance, drive air conductor 14a, exhaust air conductor 15a, and light conductor 24a) are provided with their own swivel connectors. The swivel connector 40 used for the drive air passage is shown in detail in FIG. 7 and is essentially the same in construction as swivel connector 41 for the exhaust air passage. A tubular first member 42 is connected by its barbed end 42a to the webbed portion of conduit 14. The member 42 has a cylindrical chamber 43 that receives one end of a second member 44, the second member having an annular retention collar 45. An elastomeric sealing ring 46 is also received within chamber 43 and bears lightly against the backside of collar 45. A sleeve or bushing 47 is press fitted or otherwise permanently secured within chamber 43 to retain the sealing ring 46 and the collar 45 of the second member 44 within the cylindrical chamber or socket 43 of member 42. The opposite end of second member 44 may, like member 42, be provided with a so-called barb enlargement 48 for sealingly engaging and retaining one end of the drive air conduit portion 14a.

Figure 7:
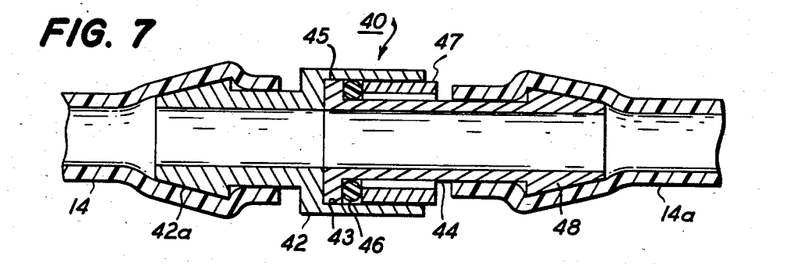
FIG. 7 is an enlarged longitudinal sectional view taken along line 7—7 of FIG. 2.

The swivel connector 40 tends to be self-sealing in use since, when the system is pressurized, members 42 and 44 are urged in opposite axial directions to cause compression of elastomeric sealing ring 46. Slight leakage of drive air (and exhaust air in swivel connector 41) may not be objectionable, but such leakage may be substantially if not completely eliminated by adjusting the position of sleeve bushing 47 during manufacture to compress elastomeric ring 46 and thereby preload the system. Care should be exercised, however, to avoid preloading the system to such an extent that the torque required to cause swivel action is increased to an objectionable level. In general, the preload should not increase torque under non-pressurized conditions to a level exceeding 0.5 inch ounces. Preferably, the torque required to induce swivel action should be no more than about 0.1 inch ounces.

Figure 8:
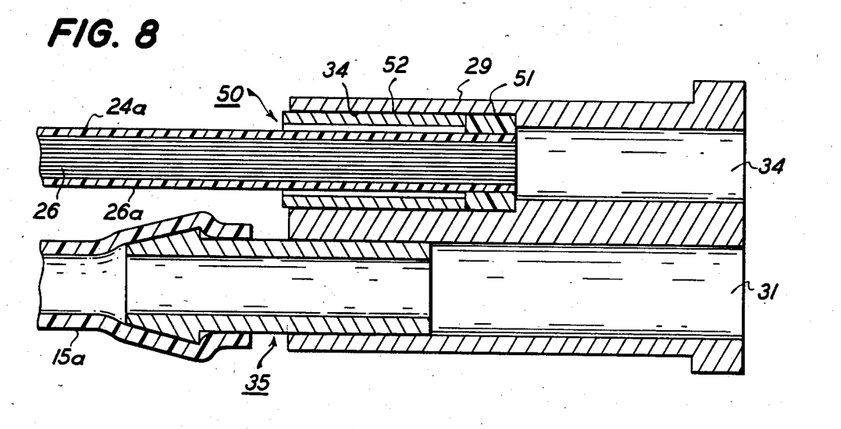
FIG. 8 is an enlarged longitudinal sectional view taken along line 8—8 of FIG. 2.
Figures 9, 10:
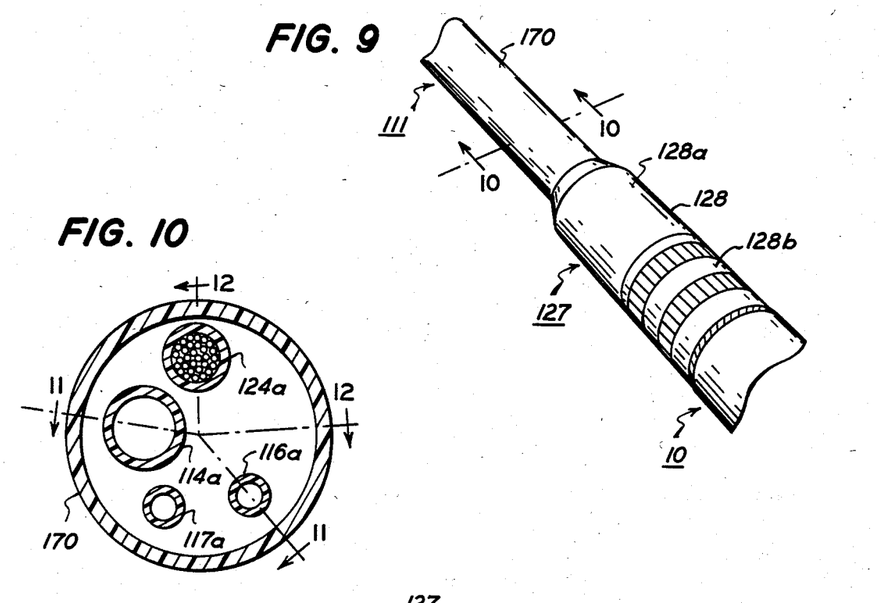
FIG. 9 is a fragmentary perspective view showing a portion of a dental handpiece hose constituting a second embodiment of this invention.
FIG. 10 is an enlarged cross sectional view taken along line 10—10 of FIG. 9.

The swivel connector 50 for the portion 24a of the light conductor may be located in the body 29 of the coupling assembly 27 as shown most clearly in FIG. 8. A retention collar 51 is secured to the end of the light conductor and a sleeve or bushing 52 is secured by press fitting or by any other suitable means within passage 34 of body 29. In securing the bushing in place, care must be exercised to avoid engaging the retention collar 51 with a force that would increase the torque requirements for inducing swivel action above the limits previously described.

The swivel connectors 40, 41, and 50 contribute significantly in reducing the torsional restraint to rotation of handpiece 10 about its longitudinal axis that would otherwise be imposed, and even more so the continual torsional restoring forces that would otherwise be generated, by the multiple-passage handpiece hose. FIGS. 2, 4, and 5 illustrate the action that occurs. In FIG. 2, the handpiece portions 14a, 15a, and 24a of the conduits or conductors are shown in a generally parallel, neutral, relaxed condition. Should the coupling element 29 be rotated one full turn in a clockwise direction, the handpiece portions of the conductors will assume the twisted appearance depicted in FIGS. 4 and 5. Since these handpiece portions are generally free of interconnecting webs, they require less torsional force to become twisted or wrapped about each other. In addition, each of the major conductors is free to swivel about its own axis and, therefore, the restraint that would otherwise be imposed in the absence of such independent swiveling action is eliminated or greatly reduced. To illustrate the extent of the swivel action of each separate conduit portion 14a and 15a, index marks 61, 62, and 63 have been applied to coupling body 29, and to the opposite ends of the free portions 14a of the air tube, and 15a of the exhaust tube, in FIGS. 2, 4 and 5. When body 29 is rotated 360° as shown in FIG. 4, so that index mark 61 again faces vertically upwardly, the index marks 62 and 63 will be found to have rotated substantially, each about its own axis, to positions approximating those shown in FIGS. 4 and 5. Such angular displacement is permitted only because of swivels 40 and 41, and it is believed evident that if such swivel action of the drive air and exhaust air tubes were somehow prevented, then the torsional restraint imposed by the individual tubes would greatly increase the force necessary to thus rotate the coupling body 29 (and the handpiece 10 connected to it).

It is to be understood that as body 29 and handpiece 10 are rotated to twist the conduits or conductors as shown in FIGS. 4 and 5, a swivel action also takes place between the end 24a of the light conductor and the coupling body 29. Therefore, as the handpiece is rotated, although the light conductor 24a wraps about the other conductors to assume a helical configuration (FIG. 4) the light conductor itself is not forced to twist about its own axis. Hence, the light conductor's resistance to such twisting action is not transmitted to the handpiece. Not only is torsional resistance to handpiece rotation reduced, but damage to the fibers of the fiberoptic bundle 26 that might otherwise result from repeated twisting of the light conductor is avoided or greatly reduced.

In the embodiment of FIGS. 9-12, the conduits or conductors for air, water, and light are not joined together by webs but are instead separate and unattached along substantially the full length of hose 111. All such conductors are enclosed within a flexible outer tube 170. The handpiece distal end of the outer tube is connected by a coupling assembly 127 to handpiece 10 with the outer sleeve 128 of the coupling being formed in two sections 128a and 128b.

Figure 11:
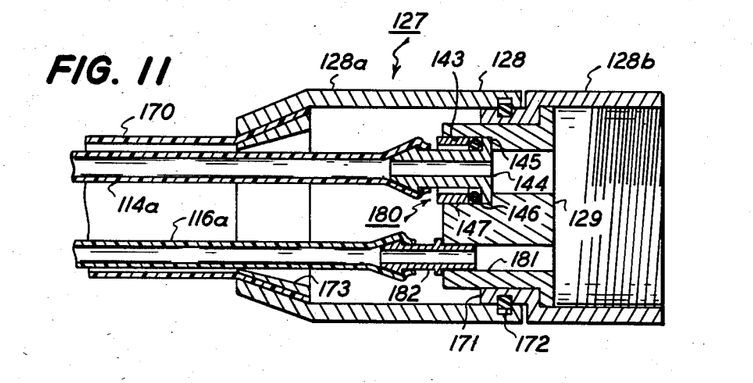
FIG. 11 is an enlarged longitudinal sectional view taken along line 11—11 of FIG. 10.

Section 128b is threadedly connected to handpiece 10. At its opposite end, section 128b is provided with a reduced collar portion 171 rotatably received within the mating end of coupling section 128a (FIG. 11). The two sections are provided with opposing grooves which receive one or more continuous connecting rings 172, the ring preferably being formed of a polymeric material that is durable, has low frictional resistance, and is capable of sealingly engaging both sections to prevent excessive leakage of air while at the same time serving as a bearing element to promote smooth swivel action between those sections. One material that has been found effective for fabrication of the ring is a polymer marketed under the designation Rulon J by Dixon Corporation of Bristol, Rhode Island, but other materials having similar properties and capable of producing similar results may be used.

The outer tube 170 has its handpiece end extending into the coupling sleeve section 128a and is securely connected thereto by means of an internal locking ring 173. The corresponding end portions of each of the separate conduits or conductors extending through outer tube 170 are connected directly to coupling body 129 which becomes locked against the rear end of handpiece 10 when sleeve section 128b is fully threaded thereon. The handpiece end 124a of the light conductor is swivel-mounted to body 129 in substantially the same manner described in connection with the first embodiment. Specifically, a swivel connection 150 is formed by providing the end of the fiberoptic bundle with a retention collar 151 rotatably received within passage 134. A sleeve or bushing 152 is secured within the passage by press fitting or by any other suitable means. The end of the light conductor is therefore freely rotatable about its own axis within the opening 134 of body 129 but is secured against longitudinal movement with respect to this body.

Figure 12:
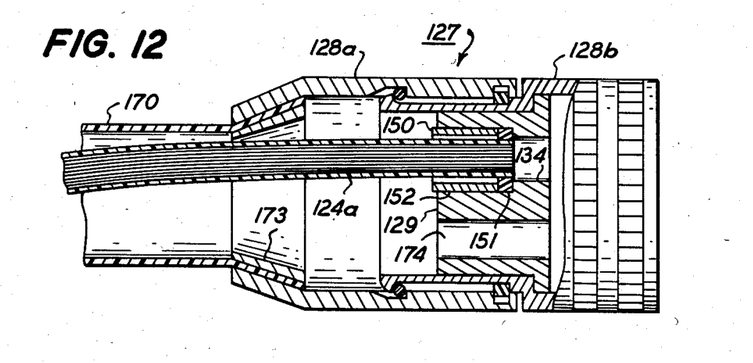
FIG. 12 is an enlarged longitudinal sectional view taken along line 12—12 of FIG. 10.

Body 129 is also provided with a bore or passage 174 for the discharge of exhaust air from the handpiece into the outer tube 170 (FIG. 12). Since the cross sectional area of tube 170 is substantially larger than the combined cross sectional areas of the conduits or conductors extending therethrough, exhaust air may flow readily away from the handpiece and through the handpiece hose.

The handpiece portion 114a of the drive air conduit is also provided with its own swivel connection to the body 129 of coupling 127. By comparing FIGS. 11 and 7, it will be seen that the swivel connection 180 is similar to swivel connection 40 except that the body 129 of coupling 127 becomes the direct structural and functional counterpart of first swivel member 42. The second swivel member 144 is retained within bore 143 of the body 129 by means of a sleeve or bushing 147, and a resilient sealing ring 146 is retained between the bushing 147 and collar 145 to prevent the escape of objectionable amounts of drive air without at the same time restraining swivel action of member 144 within body member 129. The observations previously made with regard to adjustment of torque by varying the position of sleeve 147 to control the compressing of resilient ring 146 apply equally to this embodiment.

The separate conduits or conductors 116 and 117 for transmitting chip air and water to the handpiece may be connected directly to the body 129 without the need for separate swivels, partly because of the small sizes of such conduits and also because of the importance of avoiding risks of water leakage. As shown in FIG. 11, the handpiece portion 116a of the chip air conduit communicates with a handpiece through a bore or passage 181 through body 129. A tubular barb 182 is secured within passage 181 and is received by the handpiece end of the chip air conduit in the manner illustrated. A similar connection is provided for the handpiece end 117a of the water conduit.

Rotation of a handpiece about its longitudinal axis causes the handpiece portions of the separate conduits or conductors to wrap around each other in the manner shown and described in connection with the first embodiment. In addition, the end 114a of the drive air conduit, and the end 124a of the fiberoptic waveguide, swivel about their own axes during such action, again as previously described. In addition, coupling section 128b swivels in relation to coupling section 128a, so that for limited rotation the direct torsional restraints and spring-like restoring forces that would otherwise be developed by the outer tube 170 of the handpiece hose 111 are not generated or transmitted to the handpiece, at least to any appreciable or objectionable extent.

Figure 13:
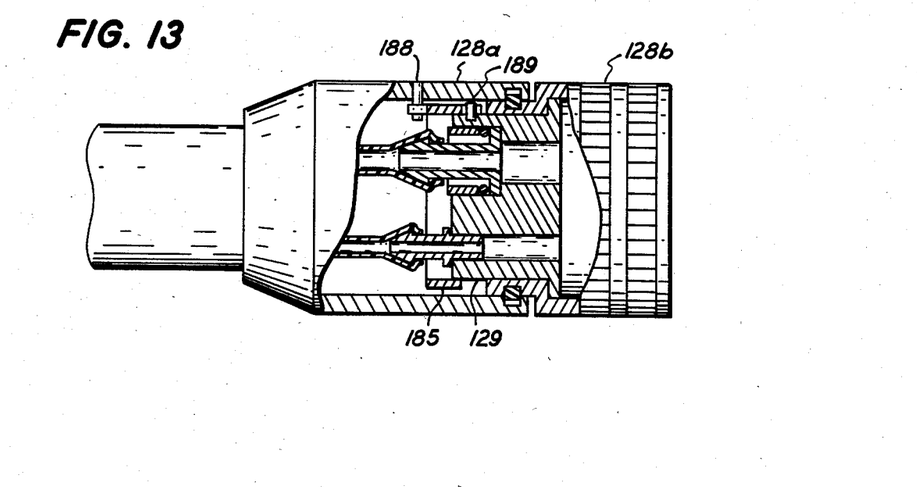
FIG. 13 depicts a modification of the construction shown in FIGS. 9-12.
Figure 14:
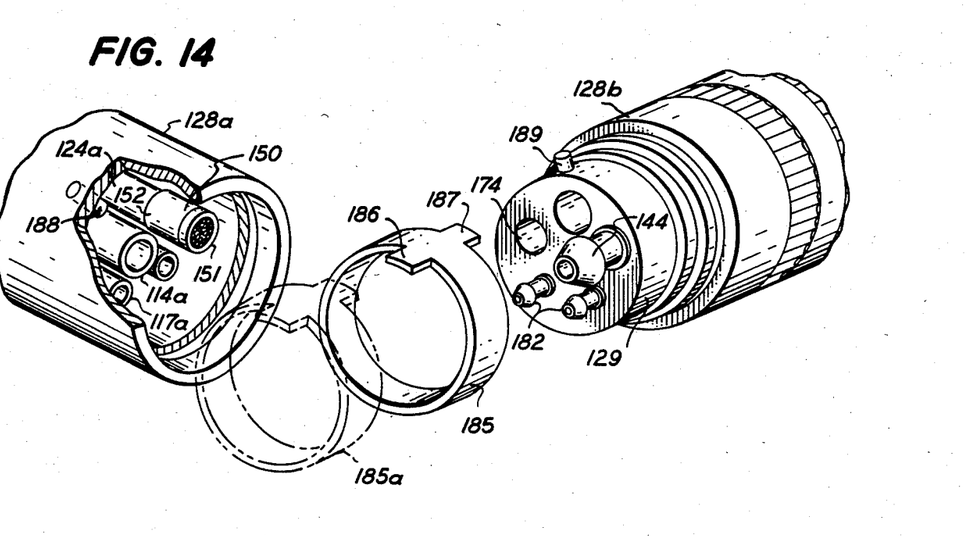
FIG. 14 is an exploded perspective view showing details of construction of the modification of FIG. 13.

Since rotation of the handpiece does cause the separate conduits or conductors to wrap (or unwrap) within outer tube 170, and since such wrapping action is concealed by the outer tube, it may be desirable to limit the extent of such action by utilizing the outer tube as a restraining means. Reference is made to FIGS. 13 and 14 which illustrate a construction identical to the embodiment depicted in FIGS. 9–11 except for the addition of a rotation-limiting ring 185 interposed between sleeve section 128a and body 129, which is in effect, an extension of section 128b. As shown most clearly in FIG. 14, the ring has a pair of arms 186 and 187 projecting axially in opposite directions from the ends of the ring. One of the arms 186 is engagable with stop means provided by coupling section 128a, such stop means taking the form of a pin 188 projecting radially inwardly from the wall of that section. The other arm 187 is engagable with stop means provided by body 129 and coupling section 128b, such stop means being in the form of a pin 189 projecting radially outwardly from the body. It is believed apparent that when the parts are coupled as shown in FIG. 13, section 128a may execute nearly one full rotation before it engages arm 186 and, similarly, body 129 and section 128b may rotate nearly one full turn in the opposite direction before being restrained by arm 187. Consequently, a handpiece, when coupled to the hose, may be rotated about its longitudinal axis nearly one full turn in either direction, or a total of almost two full turns from limit to limit, before the outer tube of the hose is forced to rotate along with the handpiece.

These effective limits of free rotation, provided by the ring 185 and its positive stops, may be extended by providing two or more such rings in tandem so that their action is additive. This is suggested in FIG. 14 by the addition, in phantom, of a second rotation-limiting ring 185a.

Figure 15:
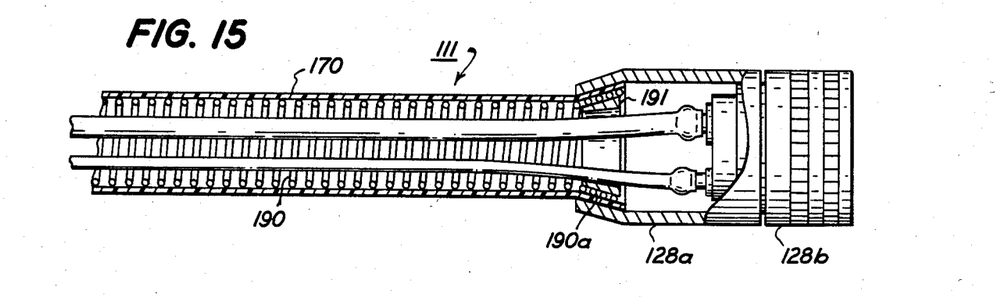
FIG. 15 shows a further modification of the hose construction of FIGS. 9-12 and 13-14.

FIG. 15 illustrates a further modification of the constructions of FIGS. 9–12 and 13–14 in which a helical spring or liner 190 is disposed within the outer tube 170 of hose assembly 111. The spring has one end 190a secured within coupling section 128a by means of locking ring 191 or by any other suitable means. The spring extends through the outer tube 170 for a distance sufficient to insure that a sharp bend will not develop in the outer tube that might otherwise interfere with the twisting and swiveling action of the conductors or conduits extending therethrough. While the length of the spring is not critical, it has been found that lengths within the range of about 6 to 12 inches are particularly suitable. The spring member 190 is only exemplary of devices that may be used to prevent flattening or buckling of the tube 170. Corrugated tubes are another example of expedients known and used for this purpose.

Figure 16:
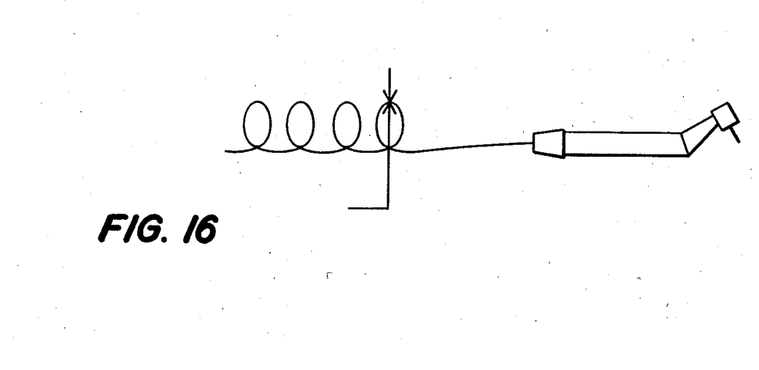
FIGS. 16, 19 and 22 represent the attitude of an instrument handpiece and hose for performing a swivel test to be described.
Figure 17:
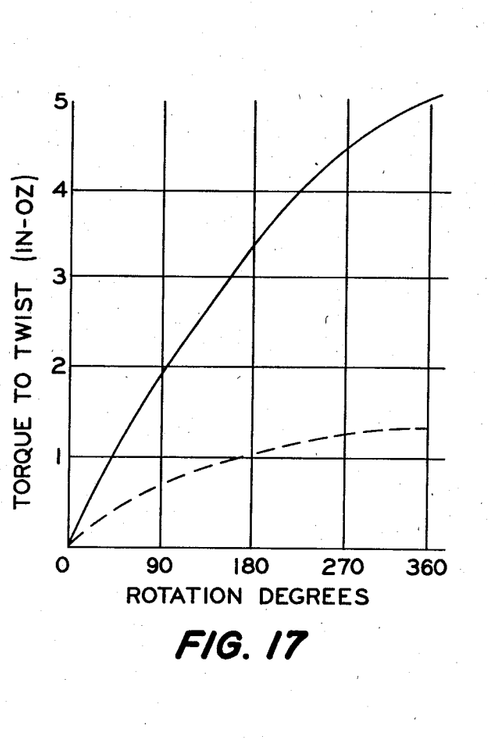
FIGS. 17, 18, 20, 21, 23 and 24 are curves of torque as a function of handpiece rotation, of prior art hoses and of the hose of this invention.
Figure 18:
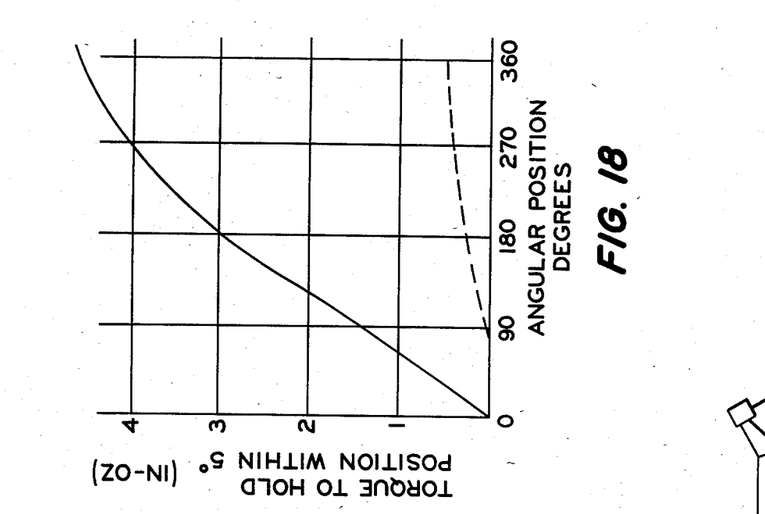
Figure 19:
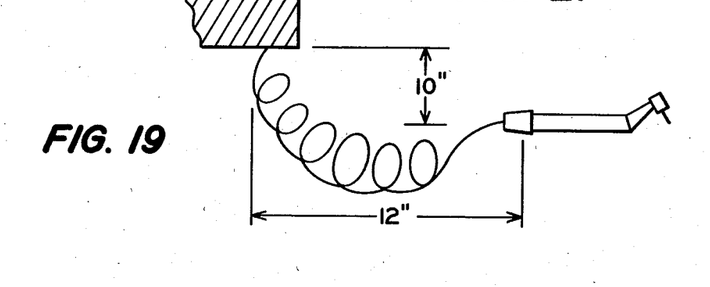
Figures 22, 23, 24:
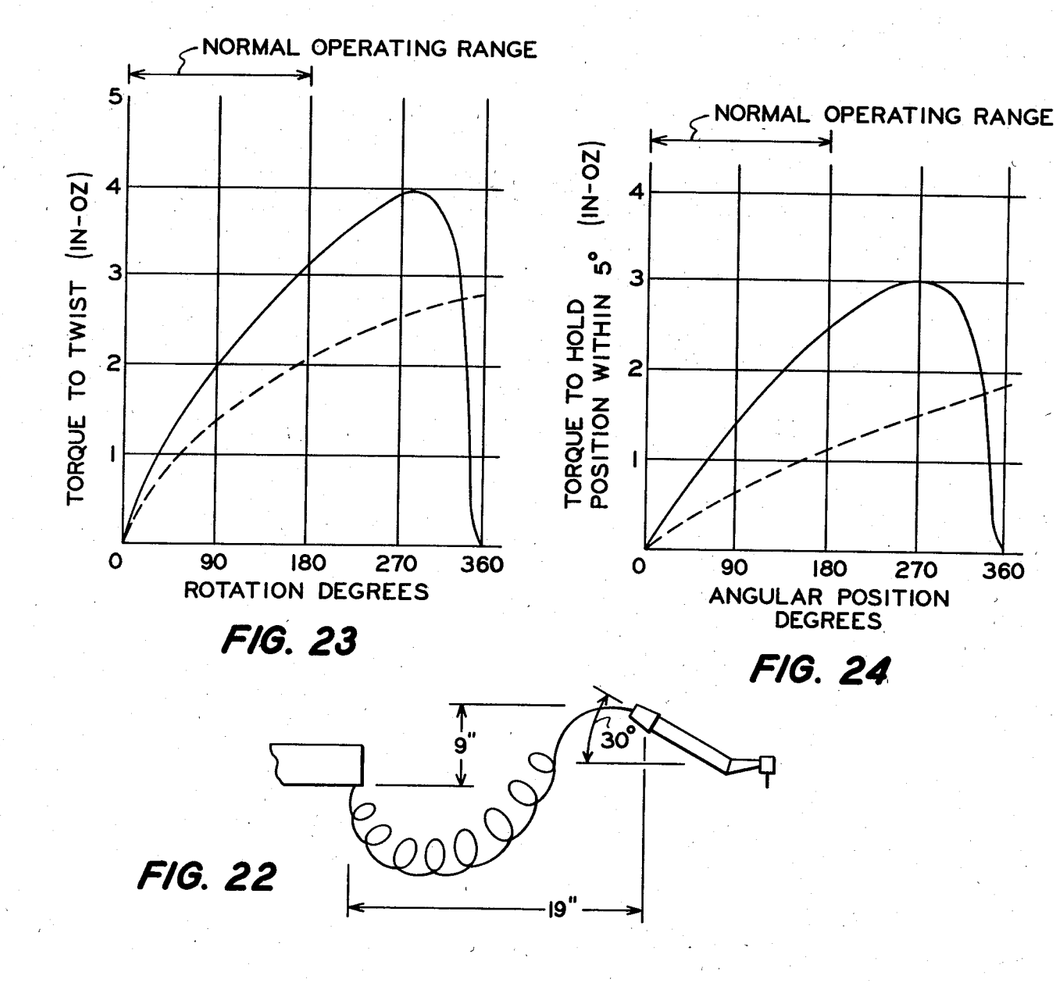

The effectiveness of this invention in reducing torsional resistance and restorative forces in a dental handpiece hose is further illustrated by the charts of FIGS. 16 through 24 as follows:

FIGS. 16, 19 and 22 represent an instrument handpiece and associated length of coiled hose. In FIG. 16, the hose was held fast at the first coil, indicated by the arrow, and the handpiece rotated 360° on its axis in each direction from a neutral position. In FIG. 17 the solid curve shows the torque required to turn the handpiece when connected to a standard prior art coiled hose and the dashed curve shows the torque required on the handpiece when connected to the hose modification of this invention. Similarly the solid and dashed curves of FIG. 18 show the torques required to keep the handpiece at the angular position indicated. The differences between the torques required by the standard hose and those required by the present invention are dramatic.

Figure 20:
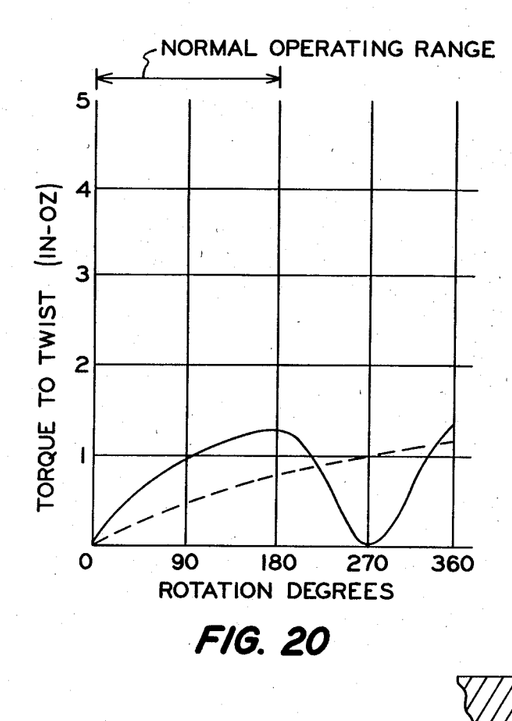
Figure 21:
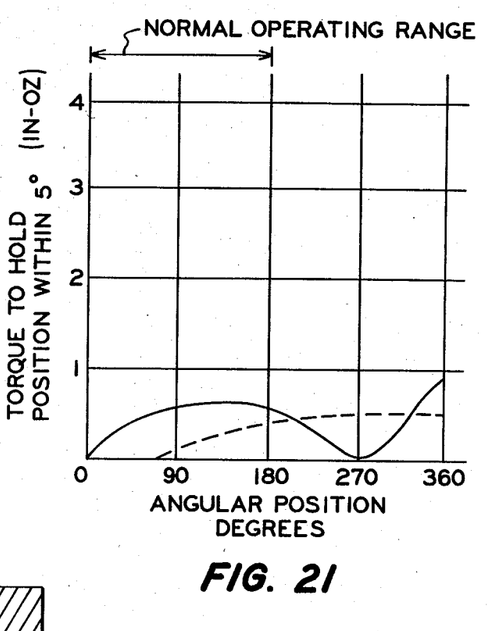

FIG. 19 represents another test condition, in which the hose is draped and anchored, and the handpiece held, as shown. The solid and dashed curves of FIGS. 20 and 21 again represent respectively a totally standard prior art hose, and the combination hose of this invention. The fact that the hose is anchored further back from the handpiece makes the results appear less dramatic because in this test condition, the effect of the standard hose is a part of the test results in each curve (remember that the improvement of the present invention is included only in a short portion immediately rearward of the handpiece—the rest of the hose back to the anchor point is standard hose). The sharp drop in the solid curve in FIGS. 20 and 21 represent flop-over of the hose at some point between 270°–360°. Incidentally, as a practical matter, the normal operating range of rotation of a handpiece is 180° in each direction from neutral.

FIG. 22 represents another test condition in which the hose is draped and anchored, and the handpiece held, as shown. The curves of FIGS. 23 and 24 are different in magnitude from FIGS. 20 and 21, but the characteristic is the same. The hose of the present invention dramatically reduces torque requirements on an operator's wrist.

The hose of this invention has been described in connection with its use as a dental handpiece hose, and it is indeed primarily useful as such. But it will be apparent that the inventive concept is not limited to such use. Other medical instruments involving handpieces and supply lines, and other instruments of a general nature involving handpieces and supply lines, are contemplated as within the intended field of use of this invention. Wherever twisting of a hose or handpiece at its working end is required, this invention may find use.

I claim:

1. A hose including a plurality of elongated and generally parallel flexible conduits or connection to an instrument handpiece, wherein the improvement comprises:

a plurality of said conduits having portions of their lengths unattached to each other for independent flexing and twisting movement of said unattached portions; and at least two of said conduits each being equipped with individual swivel connecting means permitting separate and independent swivel action of each such conduit; whereby, resistance to twisting of said hose adjacent the handpiece end thereof and the restoring torque of said hose at said handpiece end is reduced by the absence of attachment between corresponding portions of said plurality of conduits, and by the separate and independent swivel action of each of said conduits equipped with said swivel connecting means, as said conduits are twisted and untwisted about each other, said hose further including a flexible outer tube that extends at least partially along the length of said hose and contains all of said conduits, a coupling for joining said hose to said handpiece comprising a two-section swivel coupling having one section attached to said outer tube and the other adapted to be removably secured to said handpiece; said sections being generally cylindrical with one of said sections partially received by the other of said sections for free rotation with respect to each other; and retaining means for preventing longitudinal separation of said sections, said two-section swivel coupling including rotation-limiting means for limiting the extent of rotation of one of said sections with respect to the other of said sections; said rotation-limiting means comprising a ring rotatably supported on one of said sections and rotatably received within the other of said sections; said ring having a pair of arms projecting axially in opposite directions therefrom; a stop element projecting radially from one of said sections and engageable with one of said arms for limiting the extent of rotation of said section relative to said ring; the other of said sections also having a stop element engageable with the other of said arms for limiting the extent of rotation of said other section with respect to said ring.

2. The hose of claim 1 in which said rotation-limiting means comprises a plurality of said rings operatively disposed in tandem relationship so that their rotation-limiting effect is additive.

3. A hose including a plurality of elongated and generally parallel flexible conduits for connection to an instrument handpiece, wherein the improvement comprises: a plurality of said conduits having portions of their lengths unattached to each other for independent flexing and twisting movement of said unattached portions; and at least two of said conduits each being equipped with individual swivel connecting means permitting separate and independent swivel action of each such conduit; whereby, resistance to twisting of said hose adjacent the handpiece end thereof and the restoring torque of said hose at said handpiece end is reduced by the absence of attachment between corresponding portions of said plurality of conduits, and by the separate and independent swivel action of each of said conduits equipped with said swivel connecting means, as said conduits are twisted and untwisted about each other, at least one of said swivel connecting means comprising a tubular first member; a tubular second member having an annular retention collar at one end thereof; said retention collar and said one end of said tubular second member being disposed within the interior of said tubular first member for free independent relative rotation; and an annular sleeve secured within said tubular first member to prevent separation of said tubular second member therefrom, and an elastomeric sealing ring disposed within said tubular first member between the retention collar of said second member and said annular sleeve; said first and second members being urged in opposite directions in response to fluid pressure within the conductor to cause compression of said elastomeric ring between said retention collar and said annular sleeve to form a self-energizing compression seal.

* * * * *